(12) United States Patent
Wiberg et al.

(10) Patent No.: US 8,393,821 B2
(45) Date of Patent: Mar. 12, 2013

(54) SINGLE SCREW ACTIVATED DOUBLE AXLE LOCKING MECHANISM

(75) Inventors: Kristian Wiberg, Alvsjo (SE); Per Carlsson, Taby (SE)

(73) Assignee: Elekta AB (Publ), Stockholm (SE)

( * ) Notice: Subject to any disclaimer, the term of this patent is extended or adjusted under 35 U.S.C. 154(b) by 241 days.

(21) Appl. No.: 12/615,906

(22) Filed: Nov. 10, 2009

(65) Prior Publication Data

US 2010/0116278 A1 May 13, 2010

(30) Foreign Application Priority Data

Nov. 12, 2008 (EP) .................................... 08168950

(51) Int. Cl.
*F16B 7/04* (2006.01)
(52) U.S. Cl. ............. 403/388; 403/391; 403/396; 5/601; 5/622
(58) Field of Classification Search ................... 403/385, 403/388, 389, 391, 396, 398, 399; 5/601, 5/621, 622; 128/859, 861
See application file for complete search history.

(56) References Cited

U.S. PATENT DOCUMENTS

| | | | | |
|---|---|---|---|---|
| 2,295,051 A | * | 9/1942 | Roth | ............................ 403/389 |
| 2,651,026 A | | 9/1953 | Roth | |
| 2,681,058 A | * | 6/1954 | Mathues | ........................ 602/17 |
| 3,951,372 A | * | 4/1976 | Casler et al. | ................. 403/385 |
| 4,780,898 A | | 10/1988 | Sundqvist | |
| 4,782,503 A | | 11/1988 | Molitor et al. | |
| 4,951,655 A | * | 8/1990 | MacMillan et al. | .......... 128/861 |
| 5,020,195 A | | 6/1991 | LeVahn | |
| 5,242,240 A | | 9/1993 | Gorham | |
| 5,464,411 A | * | 11/1995 | Schulte et al. | ................ 606/130 |
| 6,123,482 A | * | 9/2000 | Keller | ............................ 403/384 |
| 7,025,736 B1 | * | 4/2006 | Lawrence | ..................... 403/385 |
| 2008/0247818 A1 | | 10/2008 | Oesch et al. | |

FOREIGN PATENT DOCUMENTS

CN 1926342 A 3/2007

* cited by examiner

*Primary Examiner* — Michael P Ferguson
(74) *Attorney, Agent, or Firm* — Birch, Stewart, Kolasch & Birch, LLP

(57) ABSTRACT

According to the present invention, there is provided a clamping device for locking two elements, e.g. rotatable shafts, having a substantially circular cross-section. The clamping device comprises a central holding part having two partly curved sections being adapted to at least partly encircle and hold the elements, which curved sections are inversely curved. Further, the clamping device comprises an upper holding part having a partly curved section arranged being adapted to at least partly encircle and hold a first element and a lower holding part having a partly curved section being adapted to at least partly encircle and hold a second element. The central, upper and lower holding parts are adapted to co-operate to lock the elements when pressed together by means of a tightening element. The curved sections are inversely curved in relation to each other and form together with the substantially rectangular section a substantially S-shaped central part. The invention according to the present invention is capable of locking the two elements, e.g. two rotatable spindles or shafts, firmly and accurate, i.e. without any substantial tension or torsion, by means of a single tightening element, for example, a screw.

4 Claims, 6 Drawing Sheets

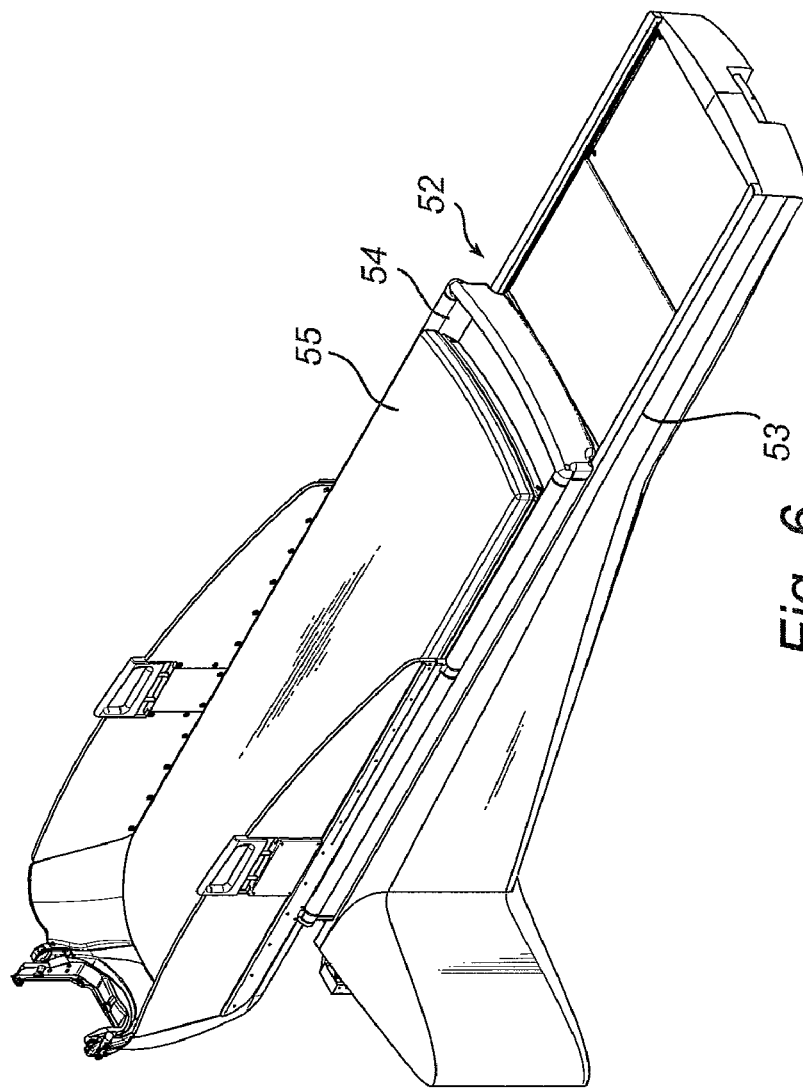
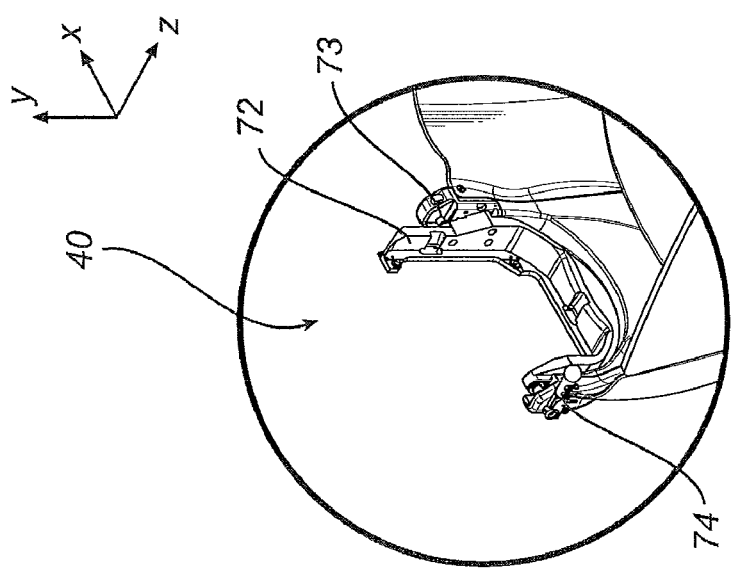
Fig. 6
Fig. 7

SINGLE SCREW ACTIVATED DOUBLE AXLE LOCKING MECHANISM

FIELD OF THE INVENTION

The present invention generally relates to clamping devices for firmly locking shafts or spindles in a accurate and tension less manner, in particular, rotatable shafts or spindles. In one specific embodiment of the present invention, the clamping device is adapted for use within the field of radiation technology, and, in particular, in a fixation device for immobilizing a head of a patient relative a treatment unit during treatment of the head.

BACKGROUND OF THE INVENTION

In many applications requiring a high degree of accuracy and reliability, such as high precision measurements or high precision treatments within the fields of fine mechanical, surveying or medical applications, it is often important to be able to securely or firmly lock shafts or spindles without any movement, e.g. translational, or rotation or turning of the shafts during the locking procedure. That is, it is important to achieve a tension less fixation of the shafts. Furthermore, it is also important in such applications to be able to firmly lock the shafts with a sufficient force to ensure that a secure and reliable locking of the shafts is achieved. Thereby, the locked position can be maintained over time until locked up to release the shafts from the fixation. One specific application with such requirements is within the field of radiation technology and, in particular, in a fixation device for immobilizing a head of a patient relative a treatment unit during treatment of the head.
The development of surgical techniques have made great progress over the years. For instance, for patients requiring brain surgery, non-invasive surgery is now available which is afflicted with very little trauma to the patient.

Stereotactic radiation surgery is such a minimally invasive treatment modality that allows delivery of a large single dose of radiation to a specific intracranial target while sparing surrounding tissue. Unlike conventional fractionated radiation therapy, stereotactic radiation surgery does not rely on, or exploit, the higher radiation sensitivity of neoplastic lesions relative to normal brain (therapeutic ratio). Its selective destruction depends primarily on sharply focused high-dose radiation and a steep dose gradient away from the defined target. The biological effect is irreparable cellular damage and delayed vascular occlusion within the high-dose target volume. Because a therapeutic ratio is not required, traditionally radiation resistant lesions can be treated. Because destructive doses are used, however, any normal structure included in the target volume is subject to damage.

One such non-invasive radiation therapy technique is so called LINAC (Linear Accelerator) radio therapy or radiation therapy. In a LINAC radiation therapy system, a collimated x-ray beam of a very high energy level is focused on a stereotactically identified intracranial target.

Another system for non-invasive surgery is sold under the name of Leksell Gamma Knife®, which provides such surgery by means of gamma radiation. The radiation is emitted from a large number of fixed radioactive sources and are focused by means of collimators, i.e. passages or channels for obtaining a beam of limited cross section, towards a defined target or treatment volume. Such a radiation device is, for example, referred to and described in U.S. Pat. No. 4,780,898.

In radiation therapy system, the head of a patient is immobilized in a stereotactic instrument which defines the location of the treatment volume in the head. Further, the patient is secured in a patient positioning unit which moves the entire patient so as to position the treatment volume in coincidence with the focus point of the radiation unit of the radiation therapy system. Consequently, in radiation therapy systems, such as a LINAC system or a Leksell Gamma Knife® system, it is of a high importance that the positioning unit which moves the patient so as to position the treatment volume in coincidence with the focus point of the radiation unit of the system is accurate and reliable. That is, the positioning unit must be capable of position the treatment volume in coincidence with the focus point at a very high precision. This high precision must also be maintained over time.

Hence, in order to obtain as favourable clinical effect as possible during the therapy is it of an utmost importance that the radiation reaches and hits the target, i.e. the treatment volume, with a high precision and thereby spares the healthy tissue being adjacent to and/or surrounding the treatment volume. To achieve this, the patient must be immobilized during a therapy session and, moreover, the position of the head of the patient must be the same in a therapy session as in a reference position, i.e. the position during the session when the pictures to create the therapy plan were captured by means of, for example, Computerized Tomography Imaging (CT-imaging). In fractionated radiation therapy where the patient is docked in and out of the radiation therapy system at each therapy session, it must thus be secured that the patient is positioned in exact the same way as in the session when the pictures were captured to create the therapy plan.

One prior art method for enabling measurements of the head of a patient and for immobilizing or fixating the head of the patient during neurological diagnosis, therapy or surgery, in particular during radiation therapy relatively an interface unit, frame or adaptor adapted to be fixated to a radiation therapy unit is a stereotactic frame provided with pin support members in form of posts having fixation pins for invasive fixation to the skull of a patient. In use during therapy or diagnostics, the stereotactic frame is arranged around the head of a patient, and the fixation pins of the posts connected to the frame are screwed into or to abutment against the bone of the skull, thus ensuring a rigid fixation of the reference system. The frame is then rigidly held in position in relation to a patient table. This kind of frame is obviously not suitable for so called fractionated therapy.

Thus, there is a need within the art of radio therapy systems for head fixation arrangements and locking devices for such head fixation arrangements that enable an accurate and repeatable fixation of a head of a patient relative a radiation therapy unit during neurological diagnosis, therapy or surgery, to secure that the patient, or more specifically the head of the patient, is positioned in exact alignment to a reference position or at a known position in relation to the reference position, and that this done every single therapy occasion of the fractionated therapy.

SUMMARY OF THE INVENTION

An object of the present invention is to provide means for firmly locking shafts or spindles relatively each other, rotational and/or translational, in a accurate and tension less manner.

Another object of the present invention is to provide a clamping device having a compact, slim, and smooth design.

A further object of the present invention is to provide a clamping device that is capable of a secure and reliable locking of shafts or spindles.

Yet another object of the present invention is to provide means for firmly locking shaft or spindles with a high clamping force and at a minimal movement of the shafts relatively each other, rotational and/or translational.

These and other objects are achieved by providing a fixation device having the features defined in the independent claim. Example embodiments are defined in the dependent claims.

It should be noted that the term "immobilizing" as used herein is intended to refer to an element, i.e. the head of the patient, that is fixated by means of mechanical means, i.e. the fixation device, to reduce or eliminate motion thereof. In other words, the immobilized head maintains its position relative to the therapy unit via interface unit or the like.

Moreover, it should also be noted that the term "treatment" as used herein, e.g. "treatment unit", "treatment system" or "treatment of the head", is intended to refer to any kind of diagnosis, therapy or surgery inside the head of the patient, e.g. MRI, Biopsy, neurological diagnosis, therapy or surgery, or various radiation therapy treatment or the like. Thus, a treatment unit may for example be a radiation therapy unit, proton therapy unit, ultrasound therapy or the like. The embodiments of the invention are suitable for a fractionated treatment, e.g. a fractionated radiation therapy.

Also, the term "medical device" as used herein is intended to refer to any kind of devices used for diagnosis, therapy or surgery inside the head of the patient, e.g. a biopsy needle or the like.

It should also be noted that the term "frame" as used herein is intended to refer to an element for supporting another element, e.g. for supporting a medical device. In such a case, the frame, for instance a stereotactic frame, provides a support for the medical device that is used for performing the treatment.

According to a first aspect of the present invention, there is provided a clamping device for locking two elements, e.g. rotatable shafts, having a substantially circular cross-section. The clamping device comprises a central holding part having a substantially rectangular section and having two partly curved sections arranged at each end of the substantially rectangular section being adapted to at least partly encircle and hold the elements, which curved sections are inversely curved. Further, the clamping device comprises an upper holding part having a substantially rectangular section having a partly curved section arranged at an end of the substantially rectangular section being adapted to at least partly encircle and hold a first element and a lower holding part having a substantially rectangular section having a partly curved section arranged at an end of the substantially rectangular section being adapted to at least partly encircle and hold a second element. The central, upper and lower holding parts are adapted to co-operate to lock the elements when pressed together by means of a tightening element.

The curved sections are inversely curved in relation to each other and form together with the substantially rectangular section a substantially S-shaped central part.

The invention according to the present invention is capable of locking the two elements, e.g. two rotatable spindles or shafts, firmly and accurate, i.e. without any substantial tension or torsion, by means of a single tightening element, for example, a screw. The inversely curved sections of the central part results in a symmetrical movement of the two elements when tightening and therefore in a minimal movement of parts being attached to the locked elements. Further advantages of the present invention are that a slim, smooth and compact design of the clamping device is achieved, which is important in, for example, applications where the available space is limited.

Moreover, the tightening element will abut on the upper and lower holding parts during tightening but not on the central holding part, which entails that the tightening force will be divided substantially equally over the upper and lower holding part, respectively.

In one embodiment of the present invention, the upper holding part is mechanically or removably connected to said central holding part by means of at least one pivot point and wherein said lower holding part is mechanically or removably connected to the central holding part by means of at least one pivot point. Due to the fact that the tightening element will abut on the upper and lower holding parts during tightening but not on the central holding part, the tightening force will be divided substantially equally over the pivot points of the upper and lower holding part, respectively.

According to one embodiment of the present invention, the upper holding part includes a through hole, the central holding part includes a through hole, and the lower part includes a threaded through hole, and wherein the central, upper and lower holding part are adapted to co-operate to lock the elements when pressed together by means of the tightening element, the tightening element being adapted to fit tight in the holes. The tightening element will abut on the upper and lower holding parts during tightening but will only pass through the central holding part, which entails that the tightening force will be divided substantially equally over the upper and lower holding part, respectively, and, in particular, over the pivot points of the upper and lower holding part, respectively.

In a further embodiment, the tightening element is a eccentric clip element enclosing the rectangular sections of the upper holding part, the central holding part, and the lower holding part.

According to a second aspect of the present invention, there is provided a clamping device for use in a fixation device for immobilizing a head of a patient relative a treatment unit or medical device during treatment of the head. The fixation device comprises a bite-block for being inserted into a mouth of the patient comprising at least one shaft/axle, wherein the fixation device may be connected to a frame adapted to be mounted in the treatment unit. The clamping device is adapted to connect a shaft, e.g. a rotatable shaft, of the frame and the shaft, e.g. rotatable shaft, of the bite-block by and the clamping device being adapted to lock the shafts so as to fixate the bite-block in a desired position in relation to the frame, which clamping device comprises a central holding part having a substantially rectangular section including a through hole and having two partly curved sections arranged at each end of the substantially rectangular section being adapted to at least partly encircle and hold the elements, the curved sections being inversely curved. Further, the clamping device comprises an upper holding part having a substantially rectangular section including a through hole and having a partly curved section arranged at an end of the substantially rectangular section being adapted to at least partly encircle and hold a first element and a lower holding part having a substantially rectangular section including a threaded hole and having a partly curved section arranged at an end of the substantially rectangular section being adapted to at least partly encircle and hold a second element. The central, upper and lower holding part are adapted to co-operate to lock the elements when pressed together by means of a tightening element being adapted to fit tight in the holes.

The clamping device in accordance with the second aspect of the present invention enables a firm and accurate locking of the two shafts, i.e. the shaft connected to the bite block and the shaft connected to the frame, without any substantial tension or torsion, by means of a single tightening element, for example, a screw. The inversely curved sections of the central part results in a symmetrical movement of the two shafts when tightening and therefore in a minimal movement of parts being attached to the locked elements. Accordingly, an accurate and repeatable fixation of a head of a patient relative a radiation therapy unit during neurological diagnosis, therapy or surgery, to secure that the patient, or more specifically the head of the patient, is positioned in exact alignment to a reference position or at a known position in relation to the reference position can be achieved. It can also be ensured that this can done every single therapy occasion of a fractionated therapy. Further advantages of the present invention are that a slim, smooth and compact design of the clamping device is achieved, which is important in, this application where the available space is limited. In addition to the advantages given above, the clamping device enables a quick and accurate fixation of the bite-block in relation to the mouth of the patient and the frame in a desired position using the easily accessible and easily maneuverable locking means of the fixation device including the clamping device. In total, the clamping device offers an accurate and repeatable immobilization of a head of the patient during treatment thereof and a tensionless fixation as well as a comfortable treatment position of the patient, which provides for a high repositioning accuracy.

According to an embodiment of the present invention, the upper holding part, i.e. the curved section, is connected to central holding part, i.e. a first curved section, by means of at least one pivot point and wherein the lower holding part, i.e. the curved section, is connected to the central holding part, i.e. a second curved section, by means of at least one pivot point. This design with locking levers, formed by the pivotally connected curved sections of the upper part and the central part and the lower part and the central part, respectively, results in a force amplification since the distance from the pivotal point to the tightening element is much larger than the distance from the pivotal point to the rotating element or axle that is to be locked.

As should be evident from this disclosure, the present invention provides a number of advantages, which many have been discussed above and will be discussed below, but, as the skilled person realizes, there are further advantages that not have been highlighted or pointed out herein. For example, the present invention provide means for an accurate repeatable fixation of a head of a patient relative a treatment unit of a head treatment system during a treatment of the head or a portion thereof, to secure that the head of the patient is positioned and repositioned in exact alignment to a reference position or at a known position in relation to the reference position every single therapy occasion of a repeatable treatment.

BRIEF DESCRIPTION OF THE DRAWINGS

It should be understood that the exemplary embodiments of the present invention as shown in the figures are for illustrative purposes only. Further embodiments of the present invention will be made apparent when the figures are considered in conjunction with the following detailed description and the appended claims.

Furthermore, it is to be understood that the reference signs provided in the drawings are for the purpose of facilitating quicker understanding of the claims, and thus, they should not be construed as limiting the scope of the invention in any way.

FIG. 6 illustrates a positioning unit used in the system of FIG. 5.

FIG. 7 illustrates a part of the positioning unit for holding a fixation device in which the clamping device in accordance with the present invention may be used.

DESCRIPTION OF PREFERRED EMBODIMENTS

Figure 1:
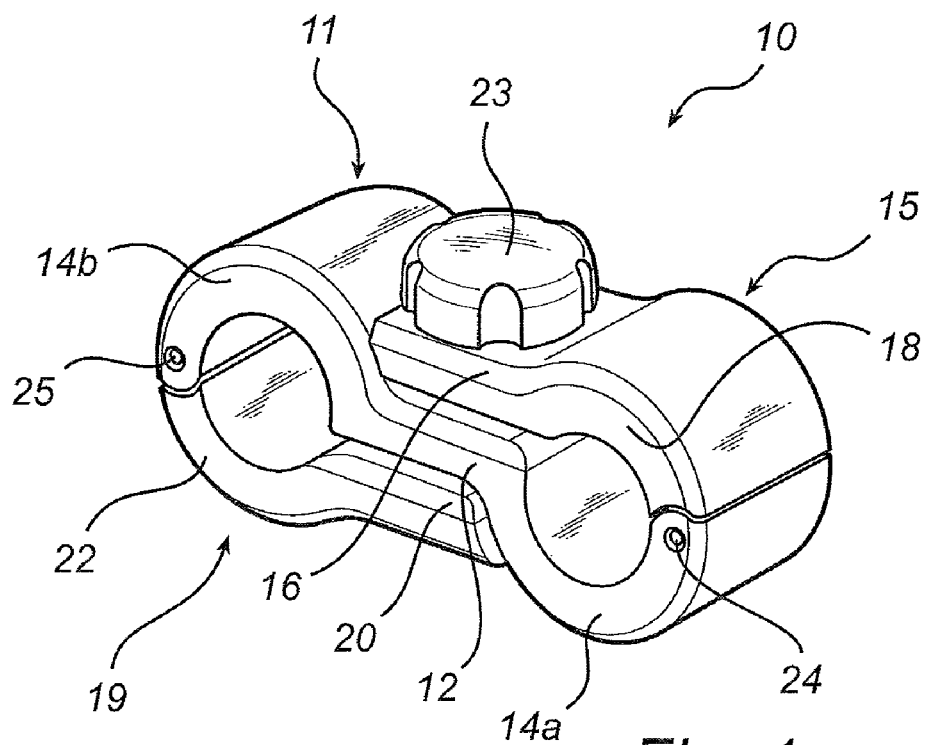
FIG. 1 schematically illustrates an embodiment of the clamping device of the present invention.
Figure 2:
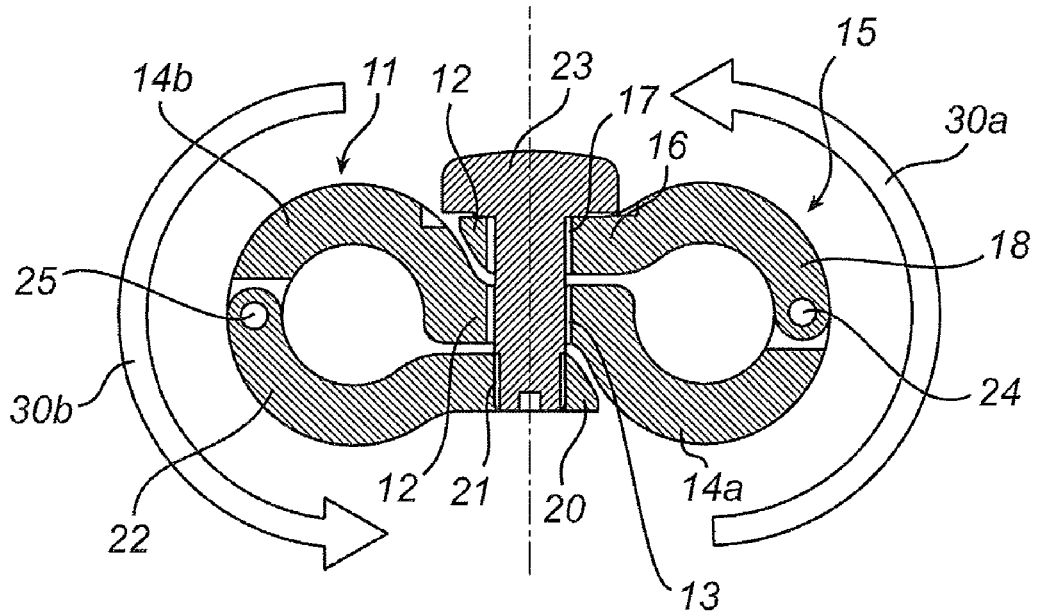
FIG. 2 schematically illustrates the principles for the clamping forces during tightening of the clamping device in accordance with the embodiment shown in FIG. 1.

First, with reference to FIGS. 1-4, a clamping device in accordance with an embodiment of the present invention and basic principles of the function of the clamping device will be discussed. In FIGS. 1 and 2, a clamping device in accordance with an embodiment of the present invention is schematically illustrated. The clamping device 10 for locking two spindles or shafts (not shown in FIG. 1, see FIG. 4 where the clamping device is shown locking two shafts 42 and 43 having circular cross sections) comprises a central holding part 11 having a substantially rectangular section 12 including a through hole 13, which may be threaded, and having two curved sections 14a and 14b arranged at each end of the substantially rectangular section 12. Each of the curved sections 14a and 14b are adapted to at least partly encircle and hold one shaft. The curved sections 14a and 14b are inversely curved in relation to each other. Thus, the inversely curved sections 14a and 14 form together with the substantially rectangular section 12 a substantially S-shaped central part 11. Furthermore, the clamping device 10 comprises an upper holding part 15 having a substantially rectangular section 16 including a through hole 17, which may be threaded. The upper holding part 15 also includes a curved section 18 arranged at an end of the substantially rectangular section 16 being adapted to at least partly encircle and hold a first shaft. Moreover, the clamping device 10 includes a lower holding part 19 having a substantially rectangular section 20 including a threaded hole 21, which may be a through hole. A curved section 22 is arranged at an end of the substantially rectangular section 20 and is adapted to at least partly encircle and hold a second shaft. The central holding part 11, the upper holding part 15 and the lower holding part 19 are adapted to co-operate to lock the shafts when tightened together or pressed together by means of a tightening element 23, which in the illustrated embodiment is a screw, being adapted to fit tight in the through holes 13 and 17, and the threaded hole 21, respectively. In embodiments, the central part 11, the upper part 15, and the lower part 19 are three separate units, where the upper part 15 can be attached to the central part 11 by means of a snap lock such that the upper part 15, or the curved section 18, is pivotally attached to the central part 11, or the curved section 14*a*. The lower part 19 may correspondingly be attached to the central part 11 by means of a snap lock such that the lower part 19, or the curved section 22, is pivotally attached to the central part 11, or the curved section 14*b*. In one embodiment, the upper holding part 15 is connected to the central holding part 11 by means of at least one pivot point 24, e.g. a pivot axis, and the lower holding part 19 is connected to the central holding part 11 by means of at least one pivot point 25, e.g. a pivot axis. Thereby, the shafts will be locked more tightly and without movement during the tightening. This is possible due to the fact that a significant force amplification is achieved, which, in turn, is caused by the fact the central part 11, the upper part 15, and the lower part 19 function as one single element, or the upper part 15 and lower 19 function as arms of lever. Further, the handling of the clamping device and the mounting procedure or tightening will also be is facilitated since the central part 11, the upper part 15, and the lower part 19 is pivotally connected as one single element.

Figure 3:
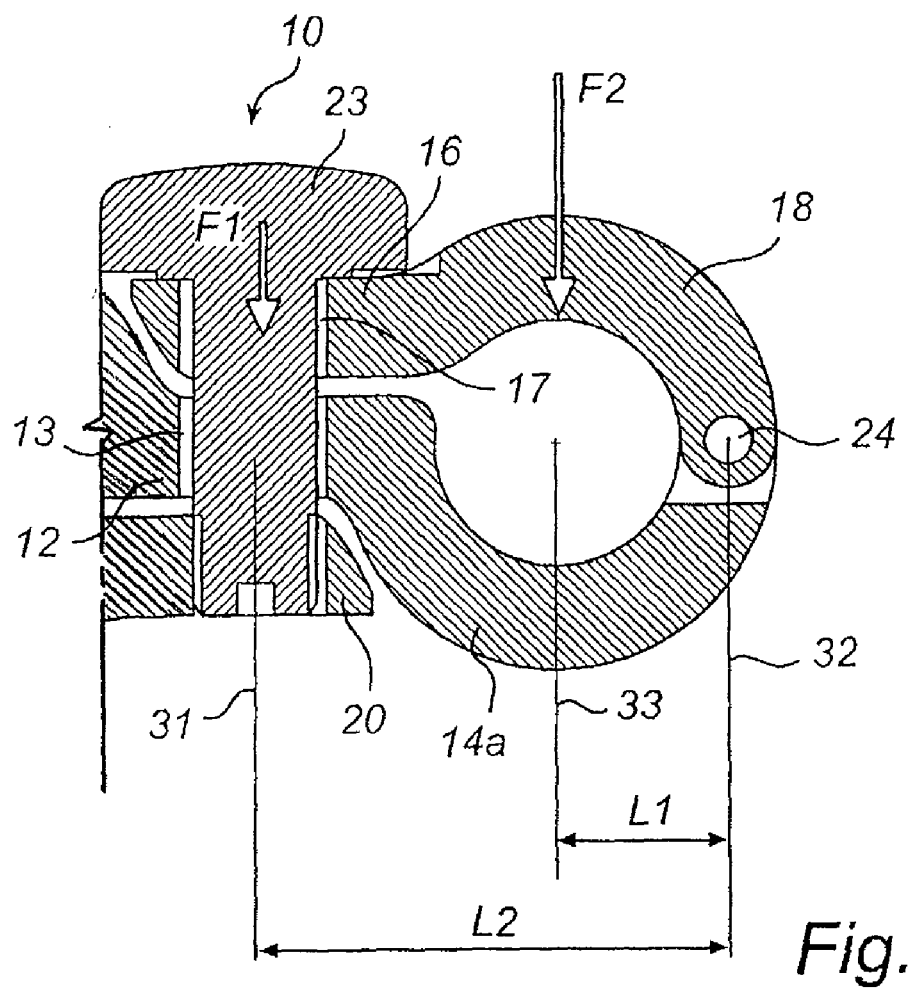
FIG. 3 schematically illustrates the principles for the force amplification during tightening of the clamping device in accordance with the embodiment shown in FIG. 1.

Turning now to FIGS. 2 and 3, the function of the clamping device according to the present invention will be described. At pressing the central part 11, the upper part 15, and the lower part 19 together by means of the screw 23, the clamping forces will work in the same clock-wise or counter clock-wise as indicated by the arrows 30*a* and 30*b* in FIG. 3. By this clock-wise or counter clock-wise coordinated working direction of the clamping forces, the clamping device 10 is capable of locking the shafts 42 and 43, see FIG. 4, significantly without relative movement of the respective shafts, either rotational (in case the shafts are rotatable) or translational, or of the parts attached to the respective shafts, which will be described in detail below. That is, since the clamping forces working in the same direction, the movement of the shafts will be minimized when tightening the clamping device to lock the shafts 42 and 43.

Figure 4:
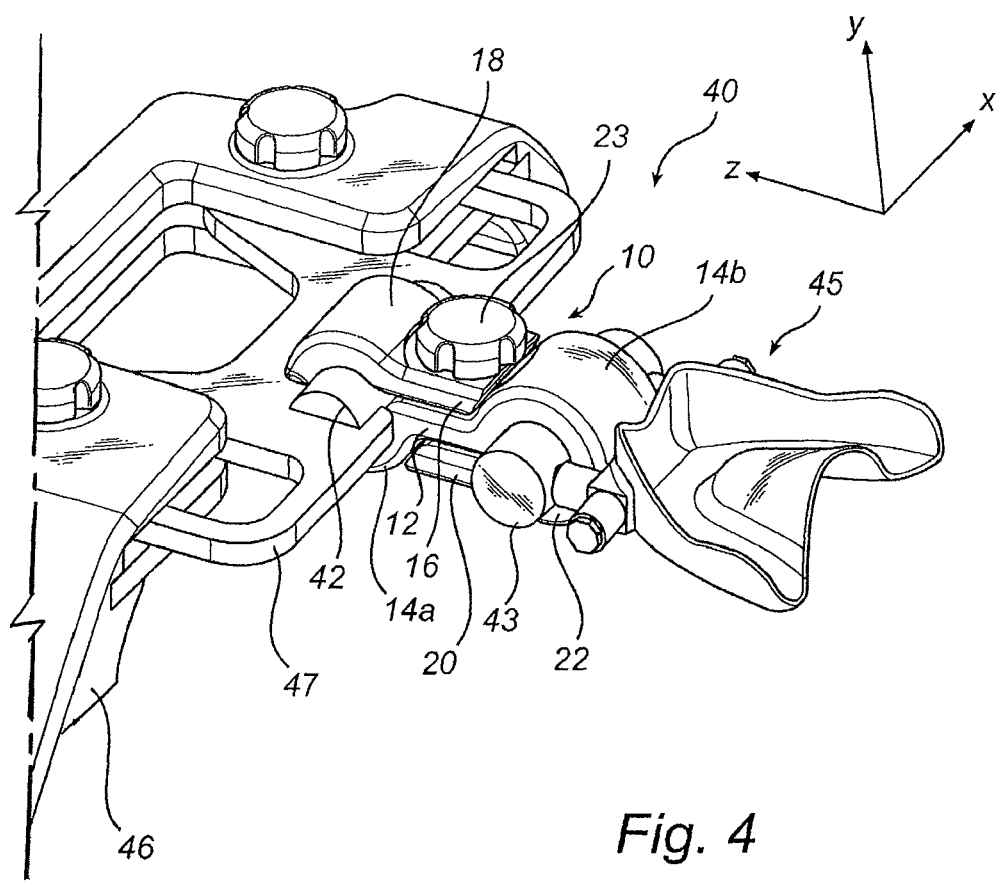
FIG. 4 schematically illustrates the clamping device in accordance with the embodiment shown in FIG. 1 used in a fixation device for a radiation therapy system.

Further, with reference now to FIG. 3, the clamping device 10 in accordance with the present invention, is capable of a significant force amplification of the force exerted by the tightening element 23 when tightening as will be discussed hereinafter. In FIG. 4, the force amplification is indicated by means of the arrows F1 and F2. This force amplification can be achieved since the arm of the lever indicated with L2, i.e. the arm of the lever corresponding to the distance between a longitudinal central axis 31 through the tightening means 23 and a longitudinal axis 32 being perpendicular to and intersecting a longitudinal central axis through the pivot axis 24 connecting the central holding part 11 and the upper holding part 15, is significantly longer than the arm of the lever indicated with L1. The arm of the lever L1 corresponds to the distance between the longitudinal axis 32 being perpendicular to and intersecting the longitudinal central axis through the pivot axis 24 connecting the central holding part 11 and the upper holding part 15 and a longitudinal axis 33 being perpendicular a longitudinal central axis of the shaft 42, see FIG. 4, being fixated by the clamping device 10 and, hence, relatively to the clamping device, when locked. Due to the symmetric design of the clamping device 10 according to the present invention, the force executed on the shaft 42 by the central holding part 11 and the upper holding part 15 will be correspond to the force executed on the shaft 43 by the central holding part 11 and the lower holding part 19.

Turning now to FIGS. 4-7, a specific application in which the clamping device 10 in accordance with the present invention may be used will be discussed.

First, with reference to FIGS. 5-7, a radiation therapy system for which the present invention is applicable comprises a radiation therapy unit or radiation unit 50 and a patient positioning unit 52 will be described. In the radiation unit 50, there are provided radioactive sources, radioactive source holders, a collimator body, and external shielding elements. The collimator body comprises a large number of collimator channels directed towards a common focus point, in a manner as is commonly known in the art.

The collimator body also acts as a radiation shield preventing radiation from reaching the patient other than through the collimator channels.

Examples of collimator arrangements in radiation therapy systems applicable to the present invention can be found in U.S. Pat. No. 6,931,096. However, the present invention is also applicable to radiation therapy systems using other arrangements for collimating radiation into a fixed focus point, such as is disclosed in U.S. Pat. No. 4,780,898. Furthermore, the present inventions is also applicable to LINAC radiotherapeutical systems, in which a collimated x-ray beam is focused on a stereotactically identified intracranial target and the gantry of the LINAC rotates around the patient, producing an arc of radiation focused on the target.

The patient positioning unit 50 comprises a rigid framework 53, a slidable or movable carriage 54, and motors (not shown) for moving the carriage 54 in relation to the framework 53. The carriage 54 is further provided with a patient bed 55 for carrying and moving the entire patient. At one end of the carriage 54, there is provided a fixation arrangement 56 for receiving and fixing a patient fixation unit or interface unit, either directly or via an adaptor unit 72, see FIG. 7.

The coordinates of the fixation unit is defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system.

The fixation arrangement 56 comprises two engagement points 73, 74, which are arranged for preventing the patient fixation unit from translational and/or rotational movement in relation to the movable carriage 54.

Figure 5:
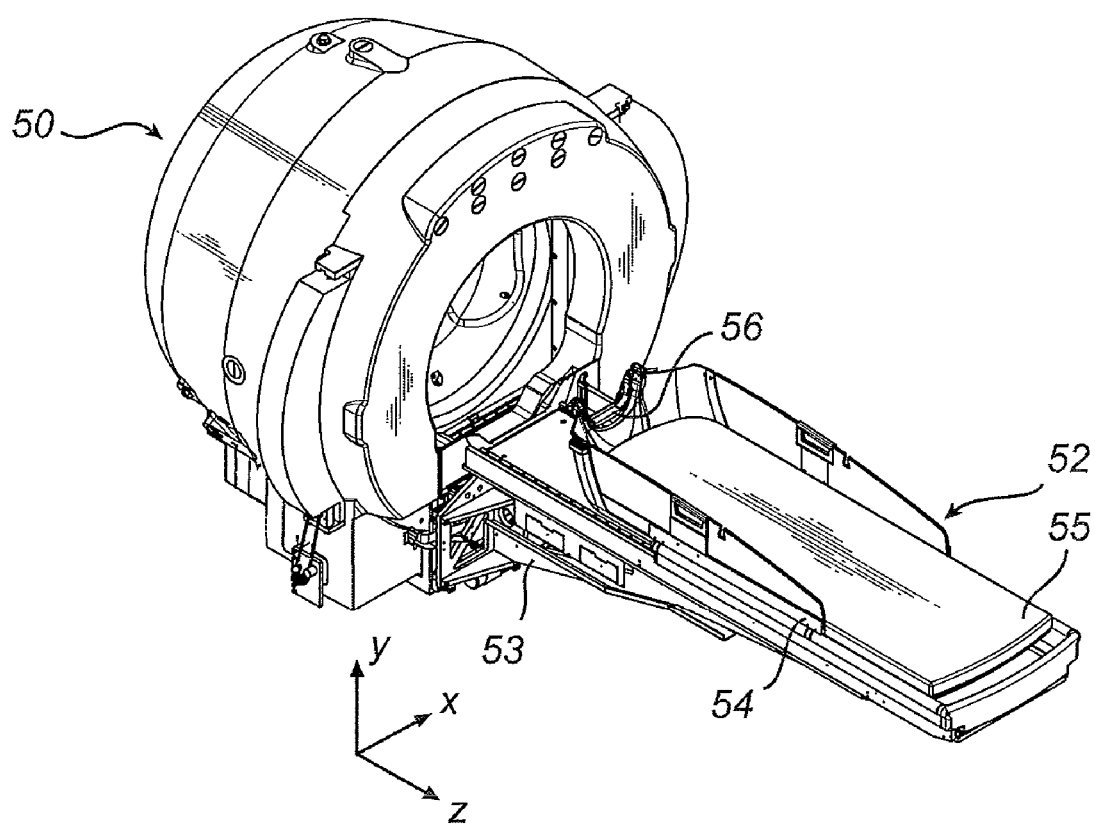
FIG. 5 illustrates the general principle of a radiation therapy system in which the present invention may be used.

As can be understood from FIGS. 5 and 6, the described embodiment concerns a radiation therapy system for providing gamma radiation therapy to a target volume in the head of human patient. Such therapy is often referred to as stereotactic radiation surgery. During therapy, the patient head is fixed in a fixation unit in the form of a stereotactic head frame, which comprises engagement points adapted for engagement with the engagement points 73, 74 of the radiation therapy system. Thus, during the stereotactic radiation surgery, the head of the patient is fixed in the stereotactic frame, which in turn is fixedly attached to the patient positioning unit via the engagement points 73, 74. During movement of the treatment volume in the head of the patient in relation to the radiation focus point, along the three orthogonal axes x, y, and z shown in FIG. 5, the entire patient is moved along the axes. Thus, there is no relative movement between the head frame and the carriage 54 of the patient positioning unit 52.

Turning instead to FIG. 4, a fixation device 40 which may be used to fixate or immobilize a patient, i.e. a head of a patient, relatively to the radiation therapy unit or radiation unit 50 and a patient positioning unit 52 during neurological diagnosis, therapy, or surgery is shown. The fixation device 40 may be connected or attached to a frame or interface unit 46, which, in turn, may be mounted via engagement points 72 and 73 and thereby fixated in relation to the radiation unit 50.

The fixation device 40 comprises a sliding part 47 including the shaft 42. The sliding part 47 enables adjustments of the position of a bite block 45 in the xz plane of a Cartesian coordinate system defined by three orthogonal axis having an x-axis extending in the medial-lateral direction of the patient, an y-axis extending in the anterior-posterior direction, and a z-axis extending in the cranial-caudal direction. The shaft 42 is parallel with the xz-plane. The bite block 45 is adapted to be inserted into the mouth of a patient to co-operate with the upper palate of the mouth (not shown). The bite-block 45 is provided with a shaft 43 being parallel with the shaft of the sliding part 47.

The shafts 42 and 43 are pivotally interconnected to each other by means of the clamping device 10, thus allowing a double-pivotal movement of the bite-block 45. In operation, i.e. when the bite-block is inserted into the mouth of the patient and co-operates with the upper palate, the bite-block 45 is pivotally movable in a plane orthogonal to the longitudinal axes of the shafts 42 and 43. By means of the clamping device 10, the shafts 42 and 43 can be locked in relation to the clamping device 10, thereby fixating the bite-block 45 in position in relation to the frame 46.

Figure 8:
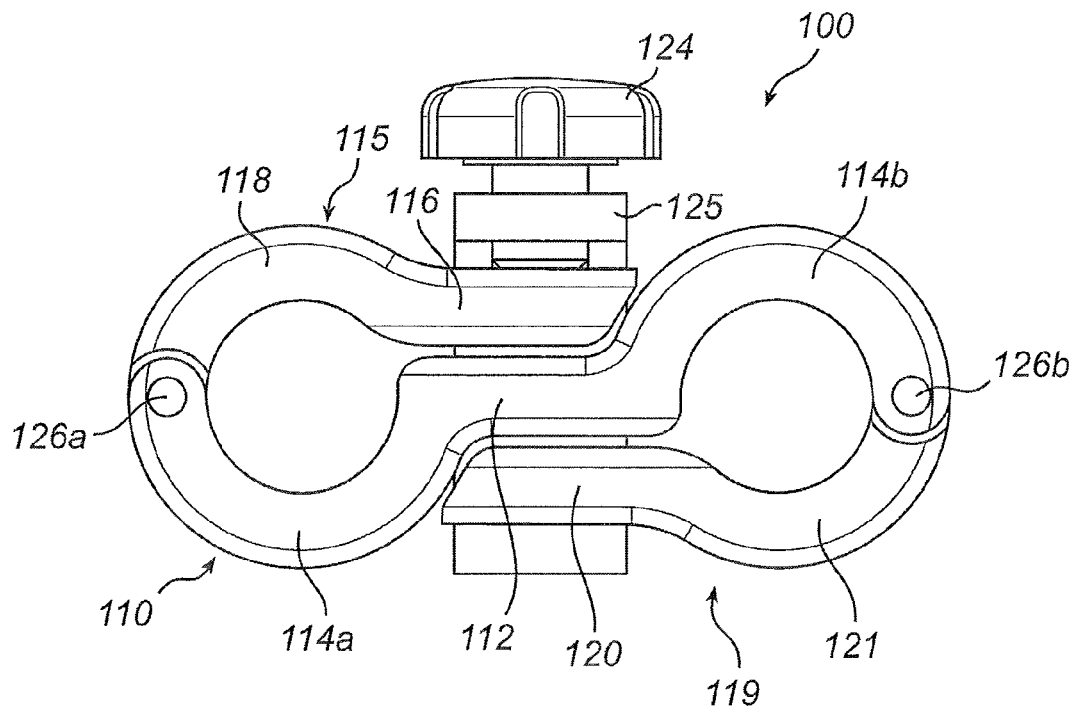
FIG. 8 schematically illustrates a further embodiment of the clamping device of the present invention.

Turning now to FIG. 8, a further embodiment of the clamping device according to the present invention will be discussed. The clamping device 100 for locking two spindles or shafts (not shown in FIG. 1, see FIG. 4 where a clamping device is shown locking two shafts 42 and 43 having circular cross sections) comprises a central holding part 110 having a substantially rectangular section 112 and two curved sections 114a and 114b arranged at each end of the substantially rectangular section 112. Each of the curved sections 114a and 114b are adapted to at least partly encircle and hold one shaft. The curved sections 114a and 114b are inversely curved in relation to each other. Thus, the inversely curved sections 114a and 114 form together with the substantially rectangular section 112 a substantially S-shaped central part 110. Furthermore, the clamping device 100 comprises an upper holding part 115 having a substantially rectangular section 116. The upper holding part 115 also includes a curved section 118 arranged at an end of the substantially rectangular section 116 being adapted to at least partly encircle and hold a first shaft. Moreover, the clamping device 100 includes a lower holding part 119 having a substantially rectangular section 120. A curved section 121 is arranged at an end of the substantially rectangular section 120 and is adapted to at least partly encircle and hold a second shaft. The central holding part 110, the upper holding part 115 and the lower holding part 119 are adapted to co-operate to lock the shafts when tightened together or pressed together by means of a tightening element 124, 125, which in the illustrated embodiment comprises a screw 124, being adapted to fit tight in a through hole of a clamp 125, which partly encloses the upper, lower and central holding parts 115, 119, and 110, respectively. The screw 124 abuts on the upper holding part 118 when tightening and the clamp 125 will abut on the upper holding part 118 and the lower holding part 119. In this embodiment, the central part 110, the upper part 115, and the lower part 119 pivotally connected to each other by means of pivot axis or articulated shafts 126a and 126b, that is, the curved section 118 is pivotally connected to the curved section 114a by means of the shaft 126a and the curved section 121 is connected to the curved section 114b by means of the shaft 126b. Thereby, the shafts will be locked more tightly and without movement during the tightening. This is possible due to the fact that a significant force amplification is achieved, which, in turn, is caused by the fact the central part 110, the upper part 115, and the lower part 119 function as one single element, or the upper part 115 and lower 119, respectively, functions as arms of lever. Further, the handling of the clamping device and the mounting procedure or tightening will also be is facilitated since the central part 110, the upper part 115, and the lower part 119 is pivotally connected as one single element.

Figure 9:
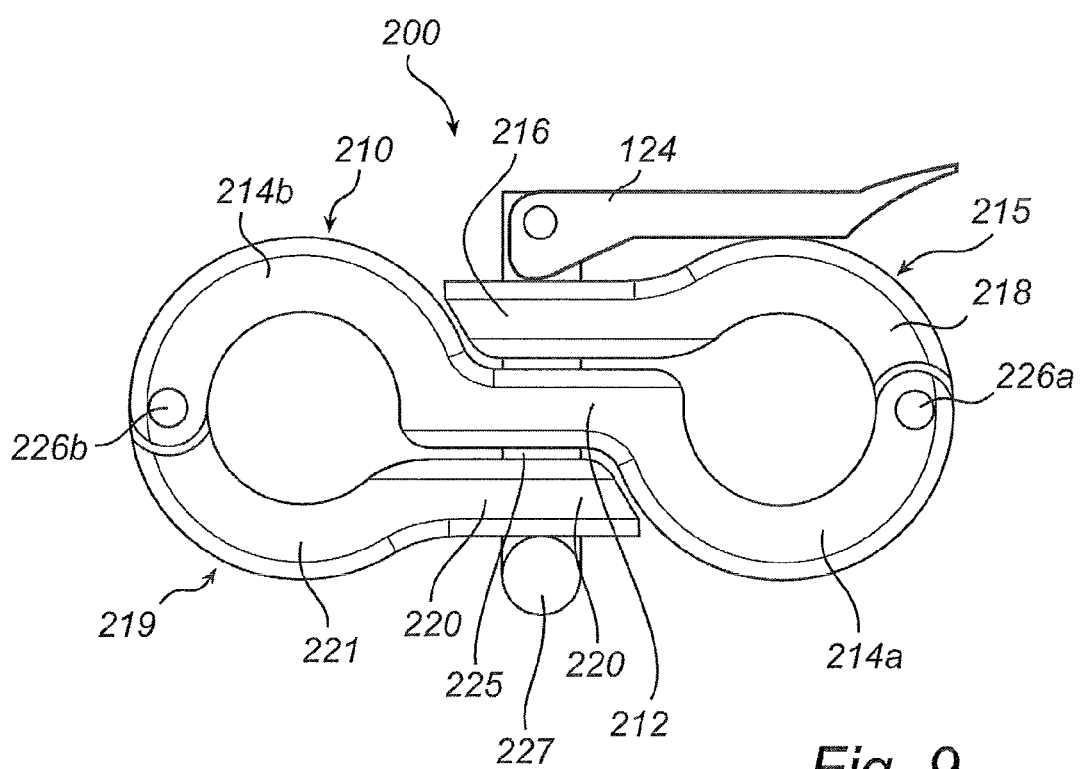
FIG. 9 schematically illustrates a another embodiment of the clamping device of the present invention.

With reference to FIG. 9, a further embodiment of the clamping device according to the present invention will be discussed. The clamping device 200 for locking two spindles or shafts (not shown in FIG. 1, see FIG. 4 where a clamping device is shown locking two shafts 42 and 43 having circular cross sections) comprises a central holding part 210 having a substantially rectangular section 212 and two curved sections 214a and 214b arranged at each end of the substantially rectangular section 212. Each of the curved sections 214a and 214b are adapted to at least partly encircle and hold one shaft. The curved sections 214a and 214b are inversely curved in relation to each other. Thus, the inversely curved sections 214a and 214b form together with the substantially rectangular section 212 a substantially S-shaped central part 210. Furthermore, the clamping device 200 comprises an upper holding part 215 having a substantially rectangular section 216. The upper holding part 215 also includes a curved section 218 arranged at an end of the substantially rectangular section 216 being adapted to at least partly encircle and hold a first shaft. Moreover, the clamping device 200 includes a lower holding part 219 having a substantially rectangular section 220. A curved section 221 is arranged at an end of the substantially rectangular section 220 and is adapted to at least partly encircle and hold a second shaft. The central holding part 210, the upper holding part 215 and the lower holding part 219 are adapted to co-operate to lock the shafts when tightened together or pressed together by means of a tightening element including a snap-lock 224, an axis 225 and a cross member 227, where the snap-lock 224 is connected to the axis 225 extending through a through hole (not shown) in the rectangular section 216, the rectangular section 212 and the rectangular section 220. The snap-lock 224 abuts on the upper holding part 218 when tightening and the cross member 227 will abut on the lower holding part 219. In this embodiment, the central part 210, the upper part 215, and the lower part 219 are pivotally connected to each other by means of pivot axis or articulated shafts 226a and 226b, that is, the curved section 218 is pivotally connected to the curved section 214a by means of the shaft 226a and the curved section 221 is connected to the curved section 214b by means of the shaft 226b. Thereby, the shafts will be locked more tightly and without movement during the tightening. This is possible due to the fact that a significant force amplification is achieved, which, in turn, is caused by the fact the central part 210, the upper part 215, and the lower part 219 function as one single element, or the upper part 215 and lower 219, respectively, functions as arms of lever. Further, the handling of the clamping device and the mounting procedure or tightening will also be is facilitated since the central part 210, the upper part 215, and the lower part 219 is pivotally connected as one single element.

Even though the present invention has been described with reference to specific exemplifying embodiments thereof, many different alterations, modifications and the like will become apparent for those skilled in the art. The described embodiments are therefore not intended to limit the scope of the present invention, as defined by the appended claims.

Furthermore, in the claims, the word "comprising" does not exclude other elements or steps, and the indefinite article "a" or "an" does not exclude plurality. Also, any reference signs in the claims should not be construed as limiting the scope of the present invention.

The invention claimed is:

1. A fixation device for immobilizing a head of a patient in relation to a treatment unit or medical device during treatment of the head, said fixation device comprising:

a clamping device for locking two elements having substantially circular cross-sections, said clamping device comprising: a central holding part having a substantially rectangular section having a first and a second partly curved sections, said first and second partly curved sections being arranged at two ends of said substantially rectangular section, respectively, wherein said first partly curved section is adapted to at least partly encircle and hold a first element, and said second partly curved section is adapted to at least partly encircle and hold a second element, said first and second partly curved sections being inversely curved;

an upper holding part having a substantially rectangular section and a partly curved section arranged at an end of said substantially rectangular section and being adapted to at least partly encircle and hold said first element together with said first partly curved section of the central holding part;

a lower holding part having a substantially rectangular section and a partly curved section arranged at an end of said substantially rectangular section and being adapted to at least partly encircle and hold said second element together with said second partly curved section of the central holding part;

wherein said partly curved section of said upper holding part is connected to said first partly curved section of said central holding part by means of at least one pivot point at one end of the central holding part, said partly curved section of said lower holding part is connected to said second partly curved section of said central holding part by means of at least one pivot point at the other end of the central holding part, and wherein said central, upper and lower holding parts are adapted to co-operate to lock said first and second elements when pressed together by means of a tightening element;

wherein said rectangular section of the central holding part overlies said rectangular section of the lower holding part and said rectangular section of the upper holding part overlies said rectangular section of the central holding part so as to form an overlapping region of said rectangular sections of each of the central, upper and lower holding parts, and wherein the tightening element extends through the overlapping region to lock the elements; and a bite-block configured to be inserted into a mouth of the patient, said bite-block comprising a shaft/axle, wherein said fixation device is structurally configured to be connected to a frame adapted to be mounted in said treatment trait, and wherein said clamping device is structurally configured to connect a shaft of said frame and said shaft/axle of said bite-block such that said shaft of said frame functions as said first element held by the clamping device and said shaft/axle of the bite block functions as said second element held by the clamping device, and said clamping device is structurally configured to lock the shaft of said frame and said shaft/axle by means of said tightening element pressing said central, upper and lower holding parts together so as to fixate the bite-block in a desired position in relation to the frame.

2. The fixation device according to claim 1, wherein said rectangular section of said upper holding part includes a through hole, said rectangular section of said central holding part includes a through hole, and said rectangular section of said lower part includes a through hole, and wherein said central, upper and lower holding part are adapted to co-operate to lock said elements when pressed together by means of said tightening element, said tightening element being adapted to fit tight in said holes.

3. The fixation device according to claim 1, wherein said central, upper and lower holding parts are adapted to cooperate to lock said elements when pressed together by means of said tightening element such that a first clamping force acting on said first element and a second clamping force acting on said second element are acting in the same clockwise or counter-clockwise direction during a tightening.

4. The fixation device according to claim 1, wherein said central holding part is substantially S-shaped.

* * * * *